(12) United States Patent
Dross

(10) Patent No.: US 8,282,643 B2
(45) Date of Patent: Oct. 9, 2012

(54) ARTHROSCOPIC METHOD AND APPARATUS FOR TISSUE ATTACHMENT TO BONE

(75) Inventor: Brian D Dross, Mt. Pleasant, SC (US)

(73) Assignee: ION Surgical Technologies, Inc., Mt. Pleasant, SC (US)

( * ) Notice: Subject to any disclaimer, the term of this patent is extended or adjusted under 35 U.S.C. 154(b) by 1335 days.

(21) Appl. No.: 11/954,612

(22) Filed: Dec. 12, 2007

(65) Prior Publication Data

US 2008/0091217 A1 Apr. 17, 2008

Related U.S. Application Data

(63) Continuation-in-part of application No. 11/157,631, filed on Jun. 21, 2005, now abandoned.

(51) Int. Cl.
*A61F 2/46* (2006.01)

(52) U.S. Cl. ...................... 606/86 R; 606/139

(58) Field of Classification Search .................. 606/79, 606/80, 86 R, 87–89, 96, 103, 104, 148
See application file for complete search history.

(56) References Cited

U.S. PATENT DOCUMENTS

| | | | |
|---|---|---|---|
| 4,265,231 A * | 5/1981 | Scheller et al. ................. 606/80 |
| 4,541,423 A | 9/1985 | Barber | |
| 4,744,353 A | 5/1988 | McFarland | |
| 4,941,466 A | 7/1990 | Romano | |
| 5,250,055 A * | 10/1993 | Moore et al. ................. 606/148 |
| 5,330,468 A | 7/1994 | Burkhart | |
| 5,562,664 A | 10/1996 | Durlacher et al. | |
| 5,575,801 A | 11/1996 | Habermeyer et al. | |
| 5,681,333 A | 10/1997 | Burkhart | |
| 5,707,350 A * | 1/1998 | Krause et al. .................... 604/22 |
| 5,782,834 A * | 7/1998 | Lucey et al. .................... 606/22 |
| 5,840,078 A | 11/1998 | Yerys | |
| 6,059,789 A | 5/2000 | Dinger et al. | |
| 6,132,433 A | 10/2000 | Whelan | |
| 6,187,011 B1 | 2/2001 | Torrie | |
| 6,238,400 B1 | 5/2001 | Bays | |
| 6,267,766 B1 | 7/2001 | Burkhart | |
| 6,524,317 B1 | 2/2003 | Ritchart et al. | |
| 6,540,750 B2 | 4/2003 | Burkhart | |
| 6,582,453 B1 | 6/2003 | Tran et al. | |
| 6,592,609 B1 | 7/2003 | Bonutti | |
| 6,692,516 B2 | 2/2004 | West, Jr. et al. | |
| 6,770,076 B2 | 8/2004 | Foerster | |
| 6,790,210 B1 * | 9/2004 | Cragg et al. .................... 606/80 |
| 6,843,796 B2 * | 1/2005 | Harari et al. .................. 606/153 |
| 6,846,314 B2 * | 1/2005 | Shapira .......................... 606/80 |
| 6,886,569 B2 * | 5/2005 | Chervitz et al. .............. 128/898 |

(Continued)

FOREIGN PATENT DOCUMENTS

| | | |
|---|---|---|
| DE | 3411891 A1 | 10/1985 |
| EP | 0081857 | 6/1983 |
| WO | WO 0067651 | 11/2000 |

*Primary Examiner* — Kevin T Truong
*Assistant Examiner* — Michael Araj
(74) *Attorney, Agent, or Firm* — B. Craig Killough

(57) ABSTRACT

Methods are described wherein bone constructs of a patient are used to arthroscopically attach sutures to torn or dysfunctional tissue. A suture or multiple sutures are passed through intersecting/bisecting tunnels formed in the bone. An end of the suture extends from each of the tunnels, and the ends are used to secure the tissue to the bone, such as by arthroscopic tying of the ends, and pulling the tissue against the bone. Devices for performing the methods are also described.

18 Claims, 10 Drawing Sheets

U.S. PATENT DOCUMENTS

| | | |
|---|---|---|
| 6,991,636 B2 | 1/2006 | Rose |
| 7,569,059 B2 | 8/2009 | Cerundolo |
| 7,771,441 B2 | 8/2010 | Cerundolo |
| 7,833,230 B2 | 11/2010 | Cerundolo |
| 7,833,244 B2 | 11/2010 | Cerundolo |
| 2002/0019634 A1* | 2/2002 | Bonutti .......................... 606/60 |
| 2003/0050642 A1 | 3/2003 | Schmieding |
| 2004/0236373 A1 | 11/2004 | Anspach, III |

* cited by examiner

ARTHROSCOPIC METHOD AND APPARATUS FOR TISSUE ATTACHMENT TO BONE

CROSS-REFERENCE TO RELATED APPLICATIONS

This application is a continuation-in-part of application Ser. No. 11/157,631 filed on Jun. 21, 2005, on which the present application is based and benefit claimed under 35 U.S.C. §119(e), is incorporated herein by reference.

BACKGROUND OF THE INVENTION

1. Field of the Invention

The invention relates to methods and devices for the arthroscopic fixation of tissue to bone using sutures. More specifically, this invention relates to a method and device for delivering sutures through bone.

2. Description of the Prior Art

Invasive and open surgery methods of attachment of tissue to bone to repair tissue is known and used. Furthermore, it is common practice to provide a passageway in a bone to reattach a torn or separated tendon to the bone. In some repair processes, foreign objects, such as suture anchors, staples or screws, are implanted and used to connect tissue to bone. An example of this method is rotator cuff surgery where the tendon may be detached or partially torn from the humerous. Thus, there is a need to overcome the invasive nature of tissue repairs by open surgical processes, and reduce the reliance on implants associated with arthroscopic repairs.

SUMMARY OF THE INVENTION

The present invention uses the bone constructs of the patient to attach sutures to torn or dysfunctional tissue. A first tunnel is arthroscopically formed in a bone. A second tunnel is arthroscopically made in the same bone and is directed to intersect/bisect the first tunnel. A suture or multiple sutures are passed through intersecting/bisecting tunnels and an end of the suture extends from each of the tunnels. The ends are used to secure the tissue to the bone, such as by arthroscopic tying of the ends, and pulling the tissue against the bone. In one aspect of the invention one of the tunnels is not linear, e.g., is curved as it passes to the intersection/bisection of the tunnels. In a preferred embodiment of the invention a suture stylus is provided for pushing sutures and knots. Another aspect of this invention is to provide an apparatus for maintaining the drill guides for each tunnel in a precise relationship so that the tunnels will be accurately placed.

BRIEF DESCRIPTION OF THE DRAWINGS

Having described the invention in general terms, reference will now be made to the accompanying drawings, which are not necessarily drawn to scale, and wherein.

DETAILED DESCRIPTION OF THE PREFERRED EMBODIMENT

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be through and complete, and will fully convey the scope of the invention to those skilled in the art.

Figure 2:
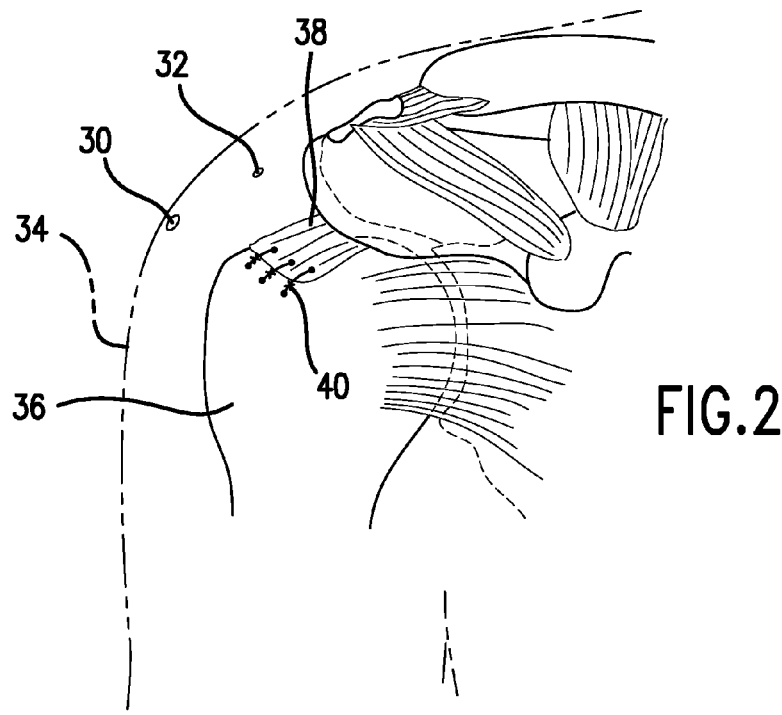
FIG. 2 illustrates three arthroscopic simple stitches, a repaired rotator cuff, and two lateral vertical portals.
Figure 3:
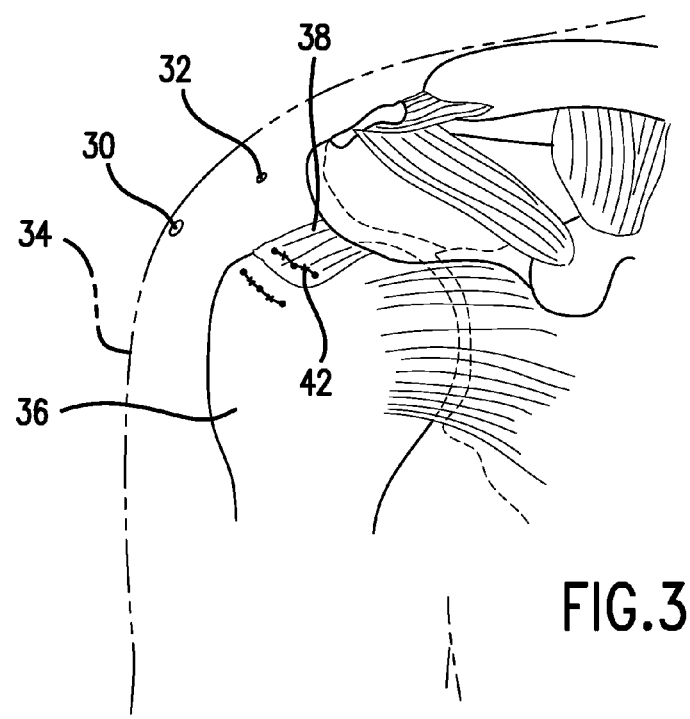
FIG. 3 illustrates two arthroscopic mattress stitches where the suture material in the bone tunnel was positioned by a suture stylus or knot pusher and was used to pass two sutures.
Figure 5:
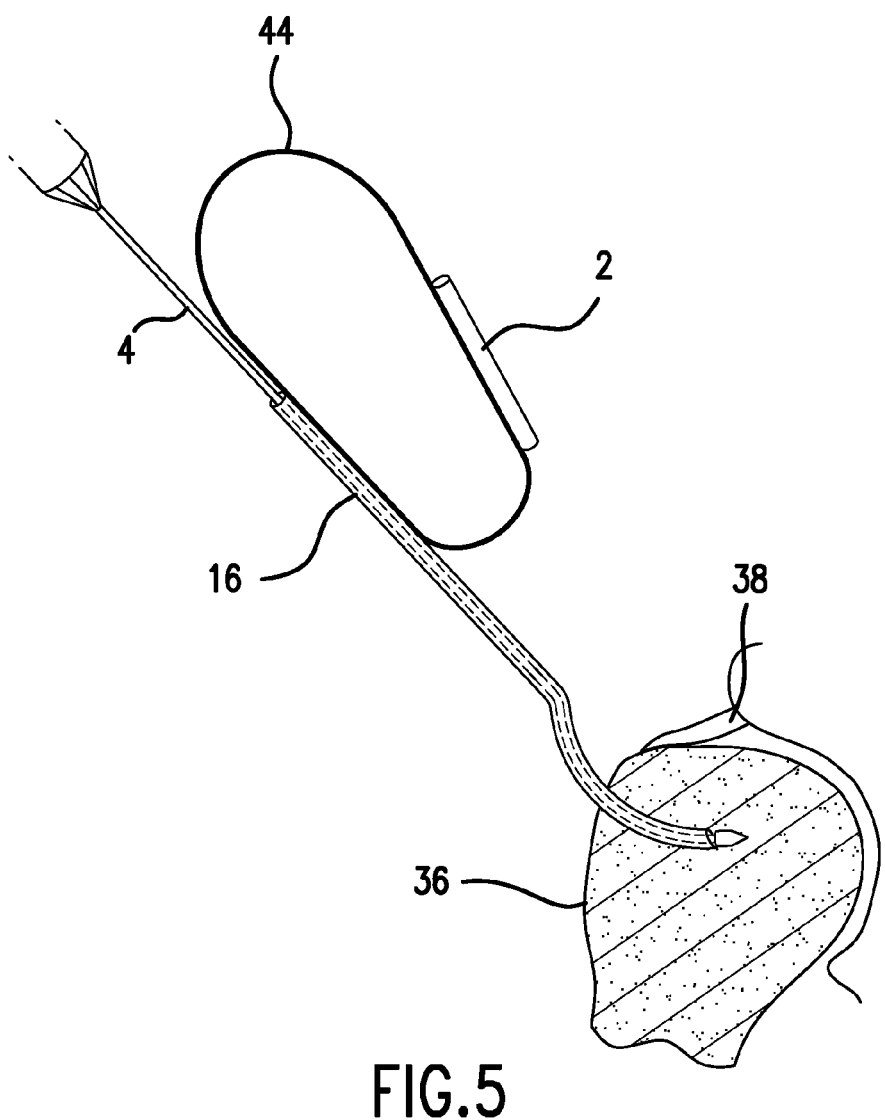
FIG. 5 illustrates insertion of the arcuate lumen rotator cuff drill guide leading with the stylus.

Referring now to the drawings there is shown in FIG. 2 and FIG. 3, a preferred embodiment of the invention demonstrating repairing a rotator cuff. Two arthroscopic portals 30, 32 are formed in the shoulder 34, such as by a scalpel. The humeral head 36 and rotator cuff tendons 38 are present. A curved or arcuate drill guide 16 having a central lumen is inserted into one of the portals, as shown in FIG. 5. The use of the arcuate drill guide is important in rotator cuff repair to miss neurovascular structures and avoid the acromion. The resulting curved tunnel also transfers biomechanical forces placed on the sutures over a radius of bone to minimize stress points on bone and suture alike. If required, cortical bone may be removed prior to insertion of the arcuate drill guide.

Figure 4A:
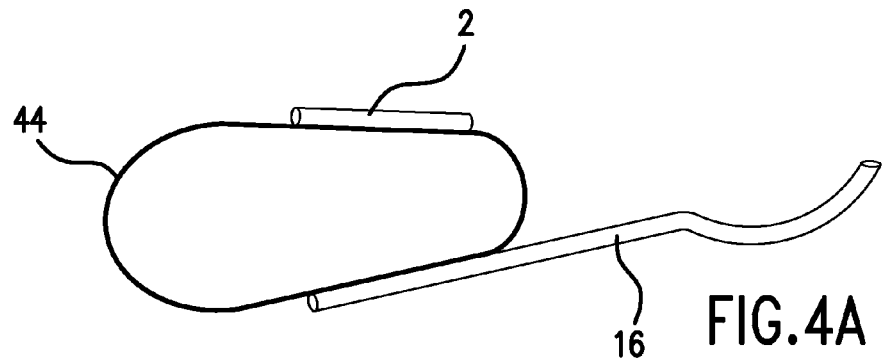
FIG. 4A shows an embodiment of a preferred drill guide assembly of the present invention having an arcuate drill guide, a straight drill guide and a handle.
Figure 4B:
FIG. 4B is a stylus for use in the arcuate drill guide having a central lumen.
Figure 6:
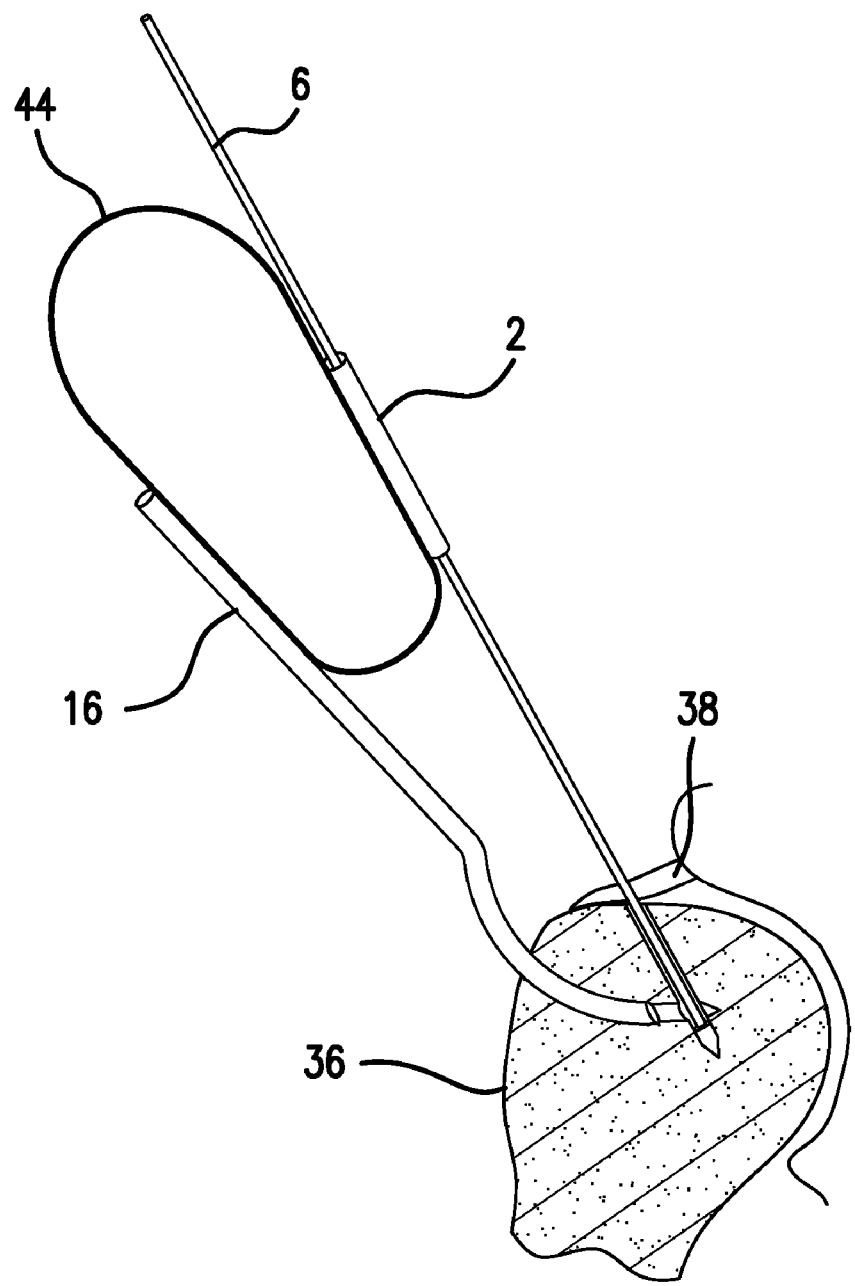
FIG. 6 illustrates the trephine guide pin that has been passed through the straight drill guide lumen.

The central lumen of the arcuate drill guide 16 has a protruding flexible stylus 4 therein that is advanced into the humeral head lateral of, or through, the torn rotator cuff. The stylus 4, shown in FIG. 4B, is formed of a memory retaining material, such as nitinol. The stylus may have a cutter formed in an end thereof, such as a drill or mill type cutter. In the embodiment shown in FIG. 4A, the forward end of the arcuate drill guide 16 is curved. Advancement of the arcuate drill guide 16 may be by manual pressure or by assisted manual force using, for example, a mallet, or by a power tool, such as a drill. The arcuate drill guide forms an arcuate tunnel in the bone. After the arcuate drill guide 16 is fully advanced, the stylus is withdrawn, leaving a small void in the bone that is present beyond the leading edge of the arcuate drill guide as shown in FIG. 5 and FIG. 6.

Figure 1:
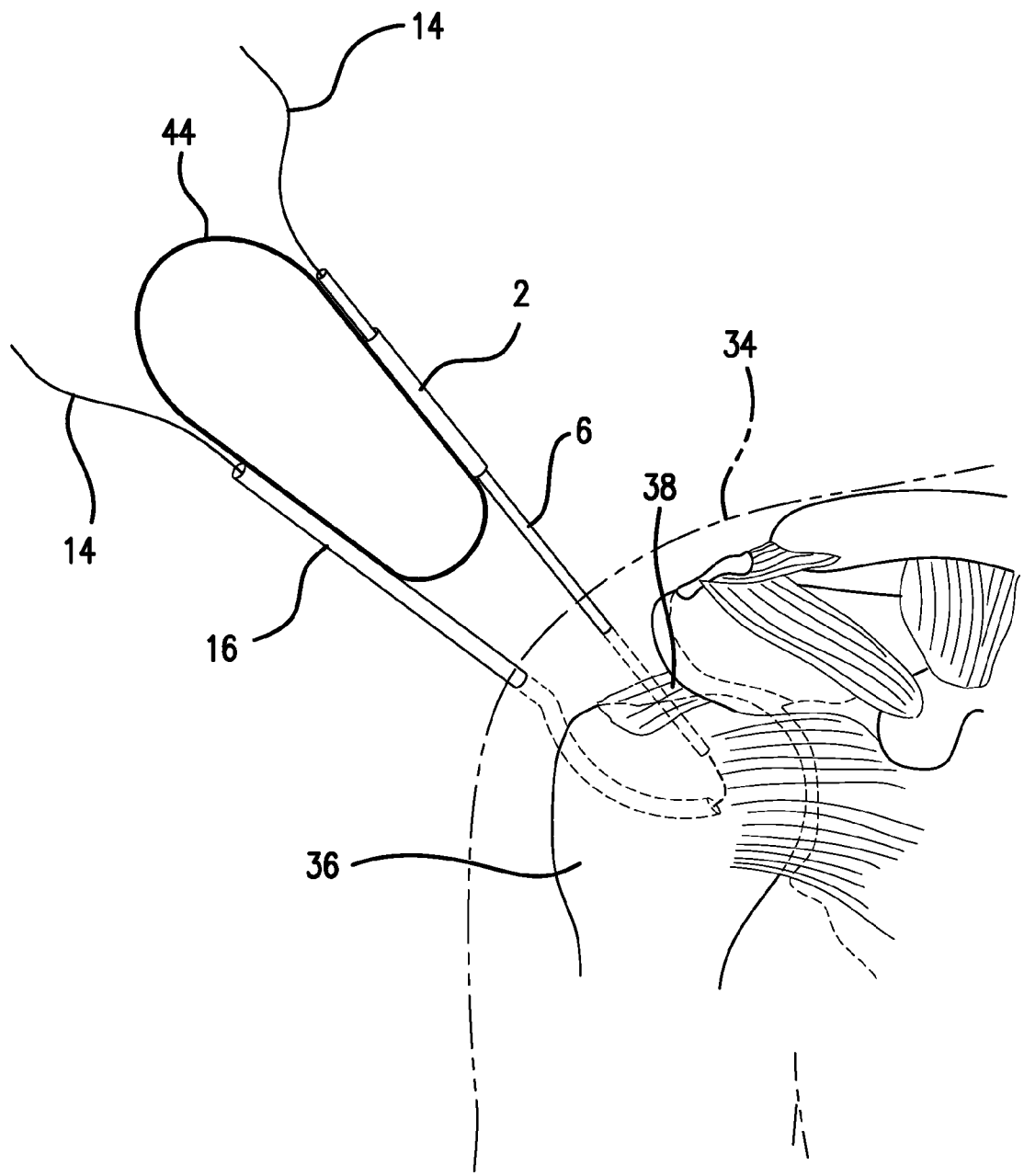
FIG. 1 illustrates a rotator cuff drill guide of the present invention in place with a trephine piercing a torn rotator cuff wherein a single stand of suture is shown passing through the drill guide, rotator cuff tissue, into and out of the humeral head, and exiting the central lumen of the trephine.
Figure 4C:
FIG. 4C is a trephine guide pin that fits into the straight drill guide lumen with enough clearance for the trephine.

As shown in FIG. 1, straight drill guide 2 is used to guide instruments through the other portal, i.e., the superior portal. The straight drill guide 2 has a lumen therein. A trephine guide pin 6 is positioned within this lumen. The guide pin may be formed of nitinol, stainless steel, or other materials well know to those skilled in the art. Sufficient space is present within the drill guide lumen for placement of the trephine guide pin 6 (shown in FIG. 4C), so that the guide pin has a sloppy fit within the drill guide. Not shown in FIG. 1 is where some rotator cuff tears would allow the curved portion of the guide 16 to also pierce the rotator cuff to achieve two suture fixation points and thus a stronger repair.

Some tears will allow neither the trephine pin 6, 8 or arcuate guide 16 to pierce the rotator cuff. A separate instrument such as a knot passer, shown in FIG. 13 and FIG. 15 or a suture passer known to those skilled in the art may be needed to pierce dysfunctional tissue.

Figure 4D:
FIG. 4D is an arthroscopic trephine.
Figure 7:
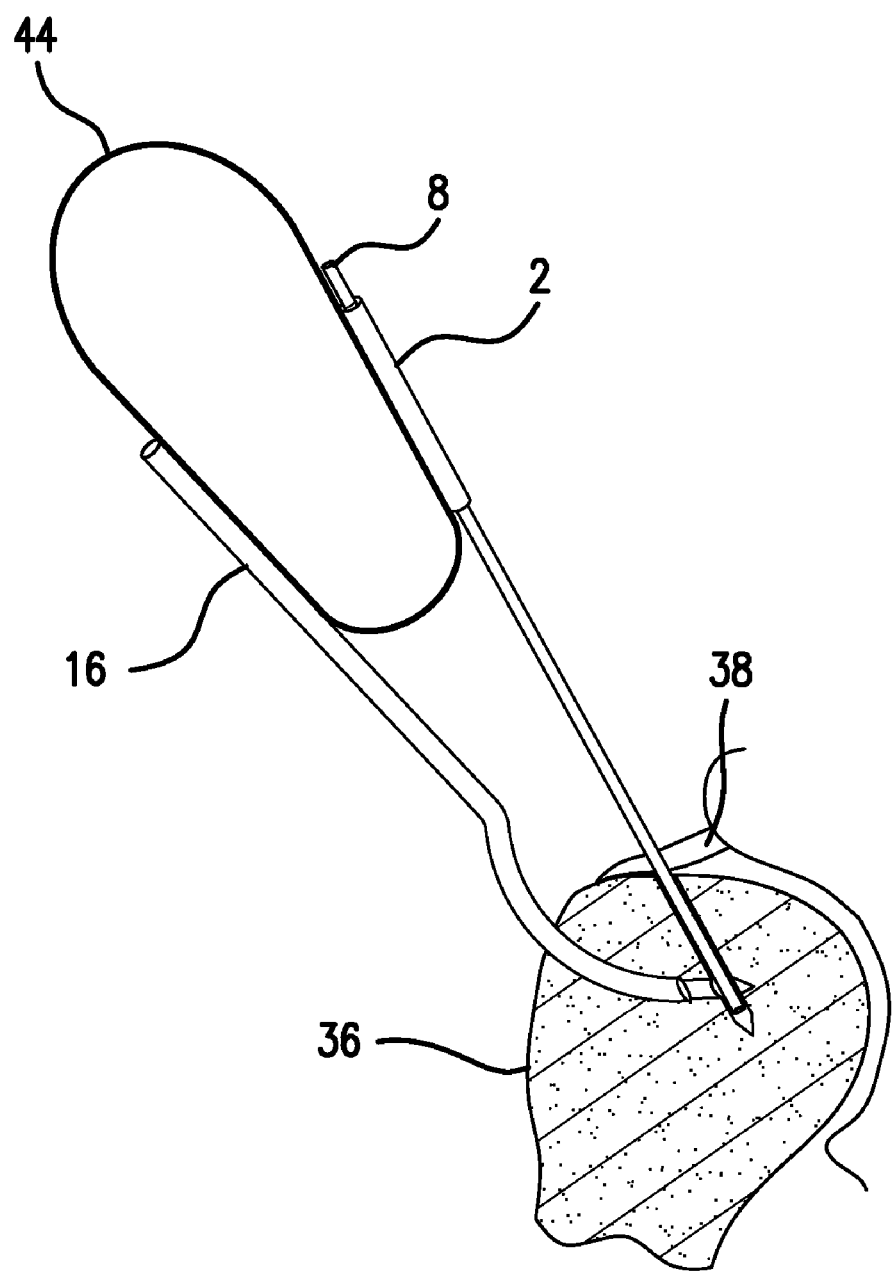
FIG. 7 illustrates the trephine inserted to a calibration point that advances the tip past the bone void left by the trephines guide pin.

The trephine 8, shown in FIG. 4D, is inserted through the lumen of straight drill guide 2. The trephine 8 has a larger diameter than the trephine guide pin 6, but will rotate within the lumen. The trephine 8 enlarges the tunnel, and is moved past the arcuate shaped tunnel formed using the arcuate drill guide 16 as shown most clearly in FIG. 7.

Figure 8:
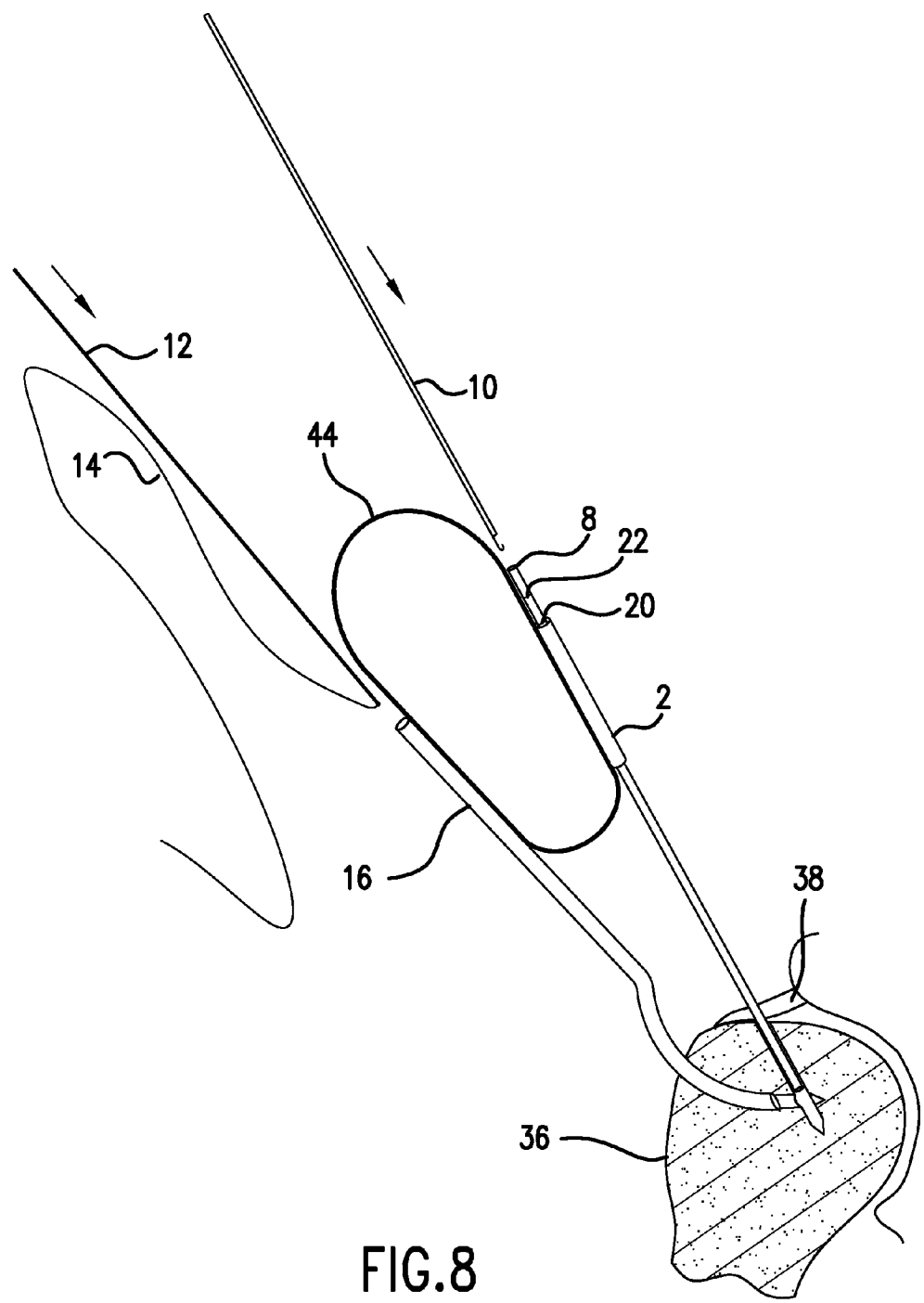
FIG. 8 illustrates the trephine partially retracted to a second calibration mark, the suture stylus with suture being advanced and the hook probe in a readied position.

In operation, the trephine 8 is retracted so that other steps may be performed. For example bone morphogenic proteins or other growth factors may be injected through the lumens. As shown in FIG. 8 the trephine may have calibration marks 20, 22 to indicate the depth of insertion and retraction of the trephine. The bone tunnels intersect/bisect as shown.

Figure 4E:
FIG. 4E is an offset hook probe that will pass into the trephine.
Figure 4F:
FIG. 4F is a suture stylus with suture loosely attached.
Figure 4F:
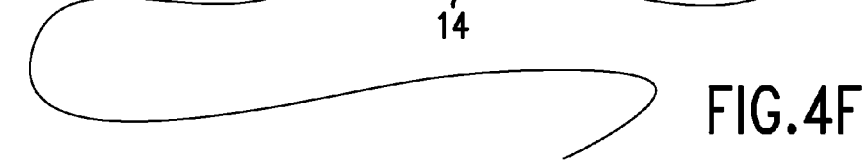
Figure 9:
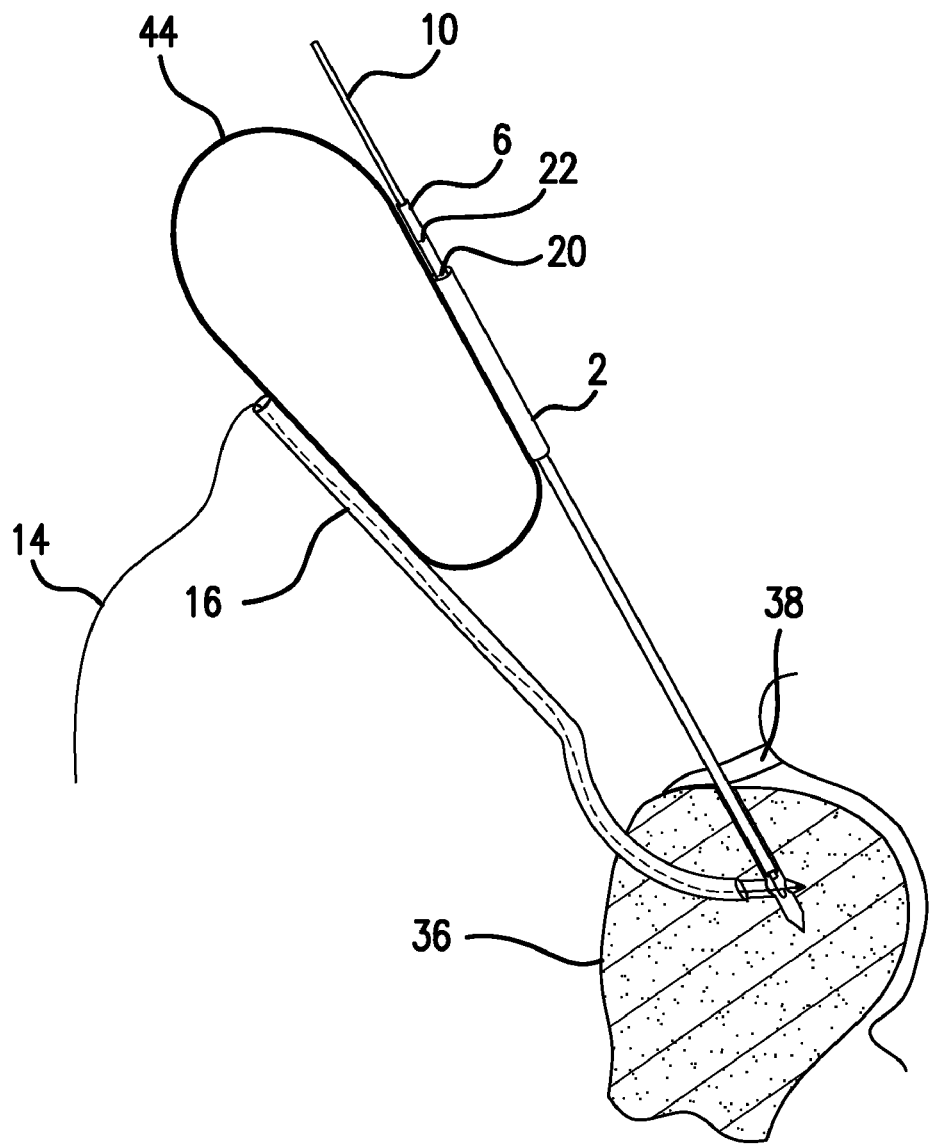
FIG. 9 illustrates the suture lodged in the bone void left by the stylus after being left behind by the suture stylus, and the hook probe which has been passed through the trephine to capture the suture.
Figure 12:
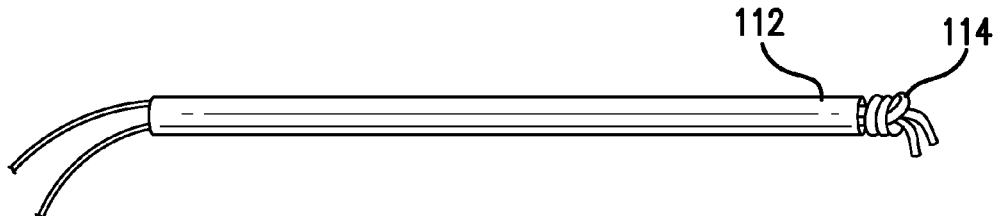
FIG. 12 is an embodiment of a knot pusher for use in the process of the present invention.

With the trephine in place, but with the stylus 4 and the trephine guide pin 6 removed from the drill guides, one or more strands of suture 14 are passed through the lumens of the drill guides, likely converging through a re-approximated rotator cuff tear, and through the two bisecting bone tunnels. The suture also passes through the humeral head (bone), and exits the central lumen. The suture or multiple sutures are advanced through the arcuate drill guide 16 by the suture stylus 12, shown in FIG. 4F or a knot pusher 112. The hook probe 10, shown in FIG. 4E shown in FIG. 12 is inserted through the lumen of the trephine to hook the suture advanced by the suture stylus 12 or knot pusher 112 at approximately the intersection of the tunnels, as shown in FIG. 9. The suture or sutures are advanced past the point of the vacated trephine tunnel.

Removal of the drill guides 2, 16 leaves the suture in place for tying. Multiple suture passes allow for tying of the suture material. For example, three (3) suture passes allow tying three (3) simple stitches 40 as shown in FIG. 2.

FIG. 3 shows two arthroscopic mattress stitches 42 where the initial suture in the center bone tunnel was used to pass two sutures. The two sutures were tied twice with their adjacent sutures to form mattress stitches. Alternatively, the outside suture strands could have been used to pull the corresponding central suture into the outside tunnel, resulting in one less knot left in the patient, and the opportunity to use a sliding knot.

As shown in FIG. 9, the arcuate drill guide 16 and the straight drill guide 2 may be connected by a handle 44. The handle positions the relative angles of the drill guides for forming the tunnels as described. The drill guides are positioned by the handle so that intersecting/bisecting tunnels are formed as disclosed herein. Both drill guides could be straight, with the drill guides angled in a non-parallel fashion to form intersecting/bisecting tunnels. The handle may also be used to receive and transfer a force for advancing the drill guides, such as by striking the handle with a mallet.

Benefits of the present invention over the use of suture anchors include the introduction of minimal foreign material in the patient, a larger "healing footprint" (which is variable with the distance between lumens) and the use of lumens as injection ports for plate rich/poor blood/growth factors or other growth factors. This method of arthroscopic bone/suture tunnel creation also has applications in shoulder laberal repair and posterior cruciate ligament and anterior cruciate ligament repair, without, or at least reducing, the requirement of suture anchors, staples or screws. The geometry of the apparatus relates to an arthroscopic creation of bone tunnels and simultaneous suture passing to repair a torn or partially torn rotator cuff.

Figure 10:
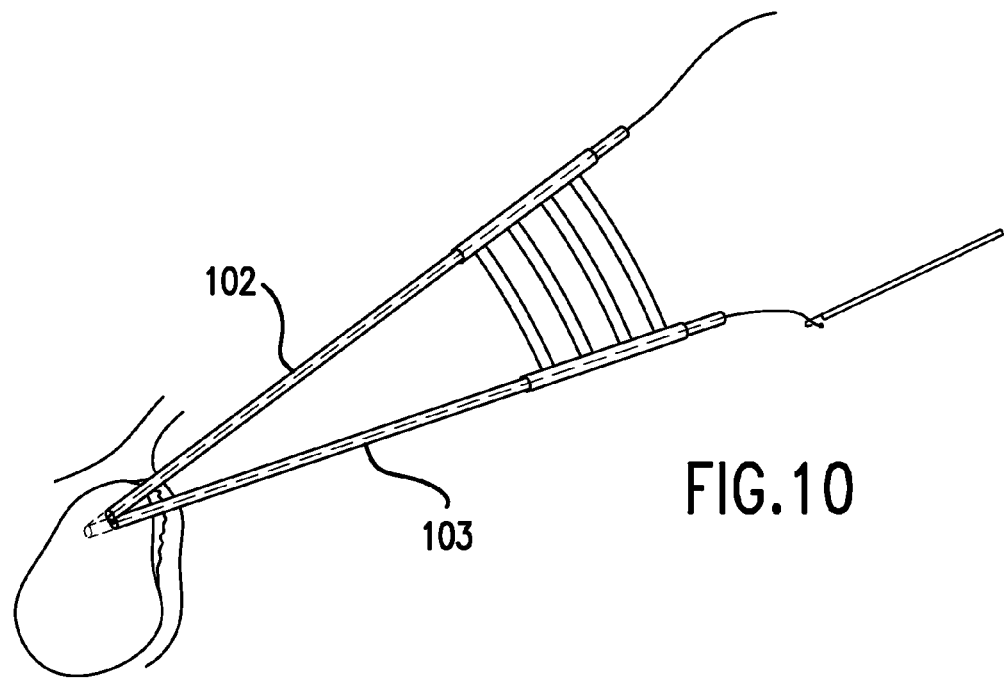
FIG. 10 demonstrates an embodiment of the device using straight, but non-parallel drill guides.

FIG. 10 shows an alternative embodiment of the present invention wherein the method of arthroscopic attachment of tissue to bone uses a different drill guide configuration to address the anatomic structure of the genohumeral joint, which are different that rotator cuff repair. FIG. 10 shows parallel drill guide lumens 102, 103 that are useful for superior labrum deficiencies or tears.

Figure 11:
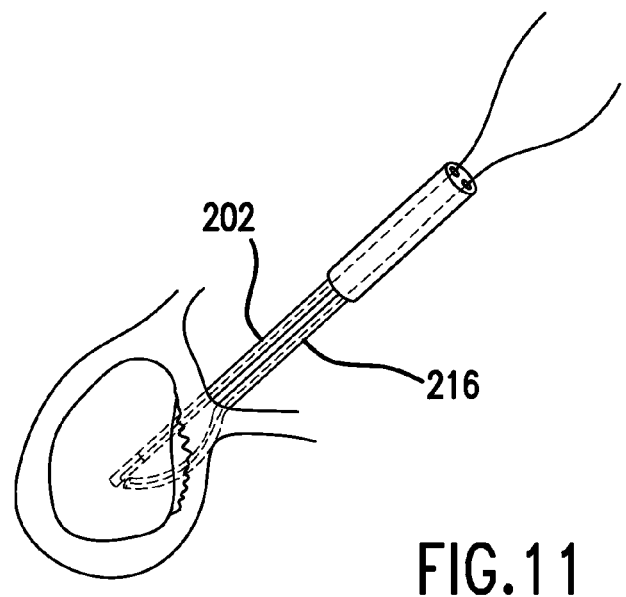
FIG. 11 demonstrates an embodiment of the device showing an additional configuration of an arcuate drill guide.

FIG. 11 shows yet another embodiment of the present invention having a drill guide that is similar to the rotator cuff guide, having one arcuate lumen 216 and one straight lumen 202 but having a different converging angle for inferior laberal repair. Aside from these differences in the apparatus, the method of arthroscopic securing tissue to the glenoid is the same as described for attaching the rotator cuff to the humeral head.

As an alternative to using the suture stylus shown in FIG. 4, there is shown in FIG. 12 a hollow tube or as is more preferably known, a knot pusher 112, of small diameter. The knot passer 112 contains a single strand or multiple strands of suture material having an enlarged end, such as a knot 114, threaded through the central lumen. As is apparent to those skilled in the art, the knot passer may be made of a rigid or flexible material. A knot 114 at the distal end of the strand or strands allows the suture to be passed into position. The tube 112 can be removed and the suture can be left behind as with the stylus of FIG. 4 or the tube 112 can be used to provide improved tactile feedback when contacting the hook probe 10, plus a means of suture protection. The suture 114 can be left in place where it is captured by a hook probe, such as shown in FIG. 4E and FIG. 9 or other suitable means known to those skilled in the art, such as a loop. The hook probe or other instrument may be in place prior to inserting the tube 112 to engage the knot/tube junction and withdraw the suture (s) from the tube.

Figure 13:
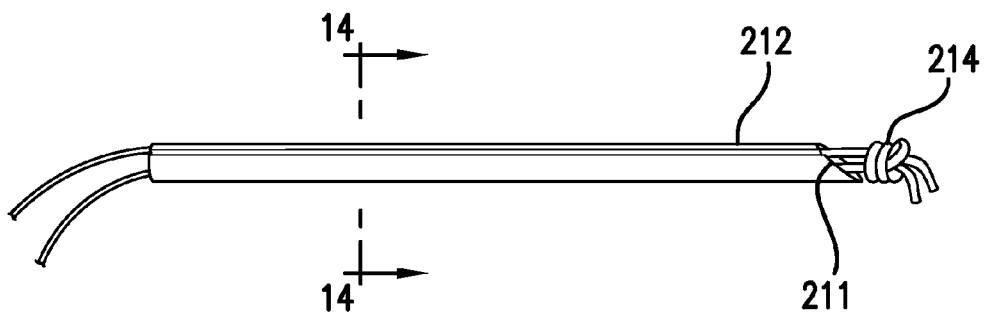
FIG. 13 is an embodiment of a knot passer having a modified distal tip and an inner knot pusher.
Figure 14:
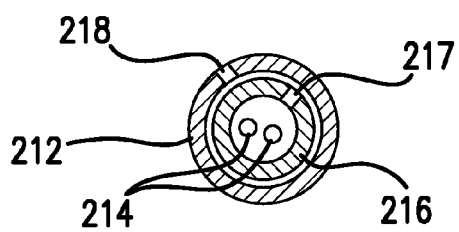
FIG. 14 is across-sectional view of the knot passer of FIG. 13 taken along line 14-14 thereof.
Figure 15:
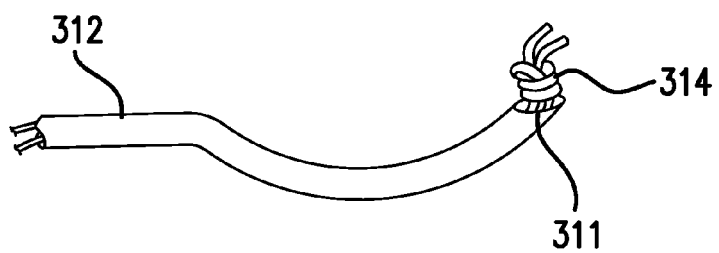
FIG. 15 is another embodiment of a knot passer having modified distal end.

FIG. 13 is an embodiment of a knot passer 212 having a modified distal tip 211 and as shown more clearly in FIG. 14, an inner knot pusher 216 having a smaller diameter that knot passer 212. This would be used to pass sutures through the tissue when neither the trephine or arcuate guide cannot reach dysfunctional tissue. The knot passer 212 contains a single strand or multiple strands of sutures 214, threaded through the central lumen. A knot formed at the distal end of the strand or strands 214 allows the suture to be pushed into position. The knot passer tip 211 may be angled to form a shape point. The knot passer 212 tube has a slot 218 running the longitudinal length of the tube as shown in FIG. 14. In a like manner, the inner knot pusher 216 has a slot 217 running the longitudinal length. When the knot passer and the inner knot pusher are rotated the slots 217, 218 are aligned so that the device may be easily removed from the sutures. In FIG. 15 there is show another modified knot passer 312 having a modified distal end 311 herein the end is curved.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of attachment of tissue to bone, comprising the steps of:
    a) arthroscopically forming a first tunnel in a bone wherein said first tunnel being arcuate from beginning to end of said first tunnel in a longitudinal direction;
    b) arthroscopically forming a second tunnel in said bone, wherein said first tunnel intersects said second tunnel;
    c) passing a suture through said first tunnel and said second tunnel, wherein an end of said suture extends from an opening to said first tunnel and an opposite end of said suture extends from an opening to said second tunnel; and
    d) securing said first end of said suture and said second end of said suture over tissue to pull said tissue against said bone.

2. The method of attachment of tissue to bone as described in claim 1, wherein at least a portion of said first tunnel is not parallel to said second tunnel.

3. The method of attachment of tissue to bone as described in claim 1, wherein said first tunnel does not pass through to an opposite side of said bone from a side of entry into said bone.

4. The method of attachment of tissue to bone as described in claim 1, wherein said first tunnel does not pass through to an opposite side of said bone from a side of entry into said bone, and said second tunnel does not pass through to an opposite side of said bone from said side of entry into said bone.

5. The method of attachment of tissue to bone as described in claim 1, further comprising forming a void in the bone at the end of at least one of said tunnels whereby said suture may be captured.

6. The method of attachment of tissue to bone as described in claim 1, wherein a portion of said first tunnel is not parallel to said second tunnel at a point of intersection of said first tunnel and said second tunnel.

7. The method of attachment of tissue to bone as described in claim 1, wherein said suture is threaded through the central lumen of a hollow stylus and said stylus containing said suture is inserted through one of said tunnels to a point where it can be engaged with a suitable instrument and the suture withdrawn from said other tunnel.

8. The method of attachment of tissue to bone as described in claim 1, further comprising introducing a biological growth factor to at least one of said tunnels.

9. A method of attachment of tissue to bone, comprising the steps of:
    a) arthroscopically forming a first tunnel in a bone using a first drill guide, wherein said first tunnel being arcuate from beginning to end of said first tunnel in a longitudinal direction;
    b) arthroscopically forming a second tunnel in said bone using a second drill guide, wherein said first tunnel intersects said second tunnel;
    c) passing a suture though said first tunnel and said second tunnel, wherein an end of said suture extends from an opening to said first tunnel and an opposite end of said suture extends from an opening to said second tunnel; and
    d) securing said first end of said suture and said second end of said suture over tissue to pull said tissue against said bone.

10. The method of attachment of tissue to bone as described in claim 9, wherein said second tunnel is formed by an arcuate drill guide lumen.

11. The method of attachment of tissue to bone as described in claim 9, wherein said first tunnel is formed by a flexible stylus that is inserted through said drill guide.

12. The method of attachment of tissue to bone as described in claim 9, wherein said second tunnel is formed by a guide pin that is inserted through said drill guide.

13. The method of attachment of tissue to bone as described in claim 9, wherein said second tunnel is formed by a trephine that is inserted through said drill guide.

14. The method of attachment of tissue to bone as described in claim 13, wherein said suture is passed through a lumen in said trephine.

15. The method of attachment of tissue to bone as described in claim 14, wherein after said trephine is trephine is fully advanced to form said second tunnel, and prior to passing said suture through said lumen in said trephine, said trephine is partially retracted.

16. A method of attachment of tissue to bone as described in claim 9, wherein said suture is threaded through the central lumen of a hollow stylus and said stylus containing said suture is inserted through one of said tunnels to a point where it can be engaged with a suitable instrument and the suture withdrawn from said other tunnel.

17. The method of attachment of tissue to bone as described in claim 9, further comprising introducing a biological growth factor to at least one of said tunnels.

18. The method of attachment of tissue to bone as described in claim 9, further comprising forming a void in the bone at the end of at least one of said tunnels whereby said suture may be captured.

* * * * *